United States Patent [19]

Broomé

[11] Patent Number: 5,009,663
[45] Date of Patent: Apr. 23, 1991

[54] METHOD FOR PERFORMING A SURGICAL CLOSURE OF A SKIN INCISION OR WOUND AND MEANS FOR CARRYING OUT THE METHOD

[75] Inventor: Albert Broomé, Helsingborg, Sweden

[73] Assignee: Brava Patient Och Invent AB, Trollhattan, Sweden

[21] Appl. No.: 497,418

[22] Filed: Mar. 22, 1990

[51] Int. Cl.$^5$ .............................................. A61B 17/00
[52] U.S. Cl. ..................................... 606/232; 606/215
[58] Field of Search ............................... 606/213–216, 606/232, 233

[56] References Cited

U.S. PATENT DOCUMENTS

| 3,648,705 | 3/1972 | Lary | 606/233 |
| 4,052,988 | 10/1977 | Doddi et al. | 606/231 |
| 4,210,148 | 7/1980 | Stirala | 606/233 |
| 4,624,256 | 11/1986 | Messier et al. | 606/230 |
| 4,788,979 | 12/1988 | Jarrett et al. | 606/230 |
| 4,791,929 | 12/1988 | Jarrett et al. | 606/228 |
| 4,825,866 | 5/1989 | Pierce | 606/216 |

Primary Examiner—Stephen C. Pellegrino
Assistant Examiner—Gary Jackson
Attorney, Agent, or Firm—Merchant & Gould

[57] ABSTRACT

A method for performing a surgical closure of a skin incision or wound in which at least one surgical suture thread is used for holding together two opposite skin edge portions. A locking device is used for carrying out the method. The suture thread is sewn through each one of the two skin edge portions and through each one of two separate elastic members arranged at the outside of a respective one of the skin edge portions. The elastic members are made of such a material that frictional forces between the elastic members and the suture thread prevent any unintentional displacement between the suture thread and the skin edge portions after the surgical closure has been completed.

10 Claims, 2 Drawing Sheets

METHOD FOR PERFORMING A SURGICAL CLOSURE OF A SKIN INCISION OR WOUND AND MEANS FOR CARRYING OUT THE METHOD

BACKGROUND OF THE INVENTION

1. Field of the Invention

The present invention relates to a method for performing a surgical closure of a skin incision or wound, and more particularly to a method in which at least one surgical suture thread is used for holding together two opposite skin edge portions of the skin incision or wound. The present invention also relates to a locking means for use in performing such a surgical closure.

2. Description of the prior art

Traditionally, skin incisions are closed by suture threads, metal clips or staples. Sutures can be used differently, either as single or running sutures, passing and knotted on the outside of the skin, thereby giving rise to more or less evident marks.

Another type of running suture is the intracutaneous or subcuticular suture. Although this suture does not give rise to any cross marks on the skin, it may influence the microcirculation of the wound or incision edges that should heal. Furthermore, applying a suture of this type is time-consuming.

Single sutures, on the other hand, are not as time-consuming and, therefore, often preferred.

Metal clips are less time-consuming and initially provide a good adaption of the skin edges. However, they must be applied quite close to each other and often leave numerous evident marks where they have penetrated the skin. Moreover, they are rather expensive.

Another drawback of using suture threads or metal clips on the outside of the skin is that the skin edge portions held together will not be fully accessible for inspection and cleaning, if required. They also prevent, at least partially, free "breathing" at the site of the closed incision.

Yet another drawback encountered in the prior art techniques described above is that none of them permits automatic compensation for the swelling normally arising during healing. More specifically, the tension forces in the suture threads or metal clips may gradually increase and give rise to unnecessarily large remaining marks.

Moreover, the tension force in a finally knotted suture thread cannot be adjusted later on during the very closure process.

SUMMARY OF THE INVENTION

It is an object of the present invention to provide a method for performing a surgical closure of a skin incision or wound which overcomes the aforementioned drawbacks of the prior art, that is a method which gives rise to no, or but very few evident marks, is inexpensive to perform, requires little time, ensures a good adaption of the skin edge portions, leaves the wound edge free and allows self-compensation and/or intra- and postoperative adjustment of the forces holding the wound edges together.

According to the invention, this object is achieved by a method comprising the steps of sewing at least one suture thread through each one of said two skin edge portions and through each one of two separate elastic members associated with a respective one of said skin edge portions and arranged at the outside thereof, said elastic members being made of such a material that when said suture thread is sewn therethrough, frictional forces are established between said members and said suture thread; and bringing together said two skin edge portions using said suture thread, said elastic members being positioned in such a relation to said suture thread that after completion of said closure, each of said elastic members is being held in contact against the respective skin edge portion by a tensioned portion of said suture thread and said skin edge portions are being held together by said tensioned portion of said suture thread;

whereby after completion of said closure said frictional forces prevent any unintentional displacement between said suture thread and said skin edge portions.

The order in which the suture thread is sewn through the two skin edge portions and through the two elastic members is optional, but in a preferred embodiment said suture thread is sewn, first through one of said elastic members, then through one of said skin edge portions, thereafter through the other of said skin edge portions, and finally through the other of said elastic members.

In a preferred embodiment of the inventive method, the two skin edge portions are finally brought or pulled together after the two elastic members have been applied to the thread. During this process of finally bringing together the skin edge portions, it is possible, with one hand, to pull in one end of the suture thread while holding with the other hand the corresponding elastic member in constant engagement against the upper face of the corresponding skin edge portion, whereby said elastic member is gradually moved along the suture thread towards the other elastic member while at the same time the portion of the suture thread located between the two elastic members is gradually shortened.

The method of the invention is particularly suitable in surgery for stitching up elongate incisions. In such a case, each of the two elastic members suitably is an elongate elastic rod having a length which preferably is at least equal to the length of the elongate incision. Each rod is disposed in parallel with the respective skin edge portion, and the suture thread is sewn through each one of the skin edge portions and each one of the rods at a plurality of points distributed at intervals along the length of the rods. A special advantage gained by this method is that the two elastic members, once they have been attached by sewing at one point, are readily accessible during the remainder of the sewing procedure.

The suture can be a running suture, or a separate suture thread can be used for each of said points.

According to the invention, there is also provided a locking means for use in performing the inventive method. The locking means of the invention is characterised by an elastic member made of a material which establishes frictional forces on a suture thread sewn therethrough.

As stated above, such an elastic member can be formed as an elongate elastic rod, especially for use in closing elongate incisions or wounds.

Since the locking means is elastic, it will readily, when being applied, conform to the outside of the skin and during the healing process follow the movements of the body and the skin without causing any discomfort to the patient.

It has been found that a generally circular cross-section is preferable for such an elongate elastic rod.

In a preferred embodiment, the elongate elastic rod having a substantially circular cross-section is provided with circumferentially opposite guiding marks for the suture thread. By means of these guiding marks, the suture thread can easily be sewn diametrically through the rod so as to prevent unintentional rotation or torsion thereof. Such guiding marks may consist of colored lines or grooves coinciding with generatrices of the rods.

The locking means of the invention may consist of any type of elastic material through which the suture thread can be shown, while giving rise to adequate frictional forces between the suture thread and the elastic material. In this context, silicone rubber has proved a useful material.

BRIEF DESCRIPTION OF THE DRAWING

These and other objects and features of the present invention will become more apparent from a consideration of the following detailed description in conjunction with the accompanying drawing in which.

DESCRIPTION OF THE PREFERRED EMBODIMENT

Figure 1:
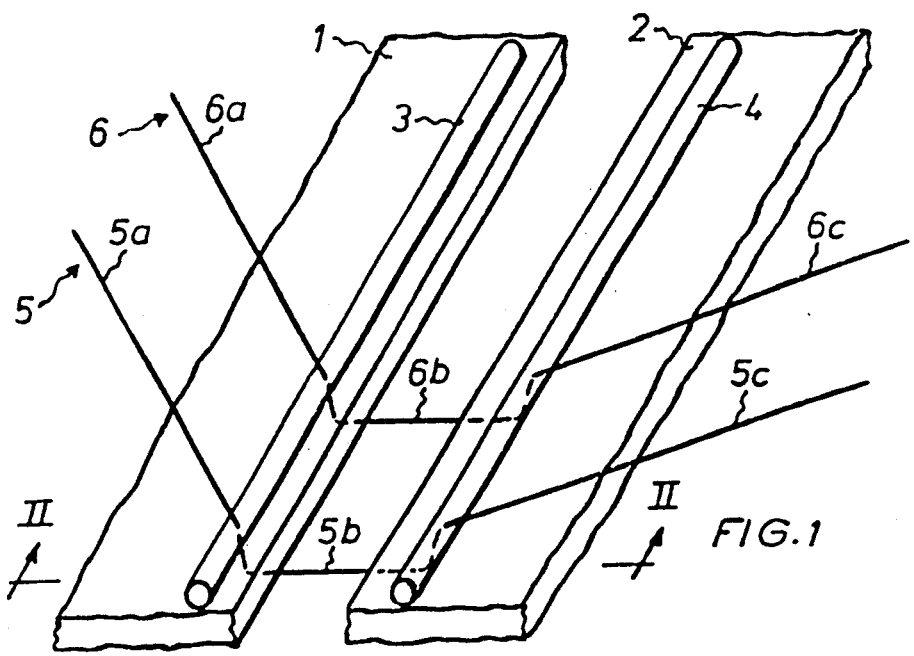
FIG. 1 is a schematic perspective view illustrating the principle of the inventive method.

In FIG. 1, two skin edge portions 1 and 2 of a surgical incision are schematically shown. Parallel to the incision and on top of each of the two skin edge portions 1 and 2, there are applied two locking members in the form of two elongate elastic rods 3 and 4, respectively, here made of silicone rubber. In the illustrated embodiment, the rods 3, 4 have circular cross-section, but other cross-sectional shapes are also conceivable.

Figure 2:
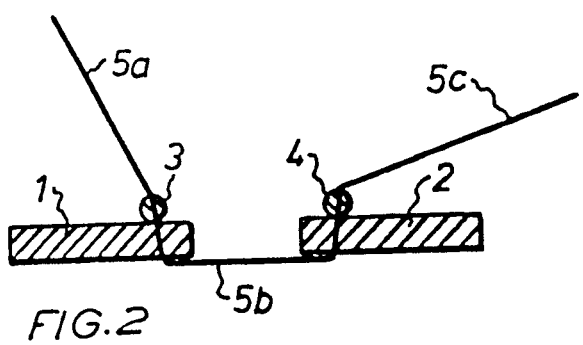
FIG. 2 is a cross-section taken along line II—II in FIG. 1.

FIGS. 1 and 2 illustrate how a suture thread generally designated 5 has been sewn through both skin edge portions 1, 2 and through both rods 3, 4. The order in which the suture thread 5 is sewn through these four parts is optional, but according to a preferred aspect of the inventive method, the suture thread 5 is sewn, first through one rod, e.g., the rod 3, then down through the corresponding skin edge portion 1, thereafter up through the other skin edge portion 2 and finally through the other rod 4. When the suture thread 5 is sewn through the first rod 3, a thread end portion 5a of e.g., 5 cm may be left. Then, the size of the frictional force between the thread and the rod material may optionally be tried. The suture thread is sewn through the first skin edge portion 1, e.g, 15 mm from the edge, and preferably down into the subcutaneous fat. The thread is thereafter sewn upwards in the same manner, through the fat, the skin 2 and the silicone rubber rod 4 on the other side of the incision.

The suture thread 5 can thereafter be cut off, e.g., 5 cm from the other rod 4, leaving a second thread end portion 5c.

Depending on the length of the incision, a suitable number of stitches can thereafter be made in the same manner throughout the length of the incision and the rods at suitable intervals as indicated by a further suture thread 6 with thread ends 6a and 6c.

Figure 3:
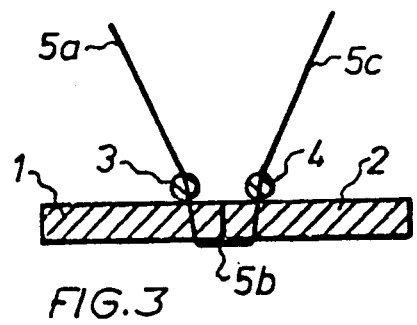
FIG. 3 is a cross-sectional view similar to FIG. 2, showing a state wherein a surgical closure has been completed.
Figure 4:
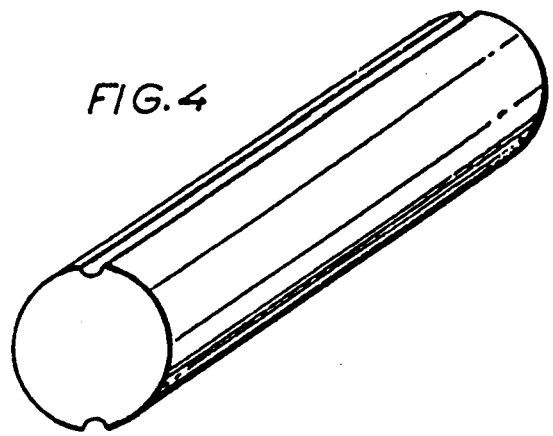
FIG. 4 is a schematic perspective view of a preferred embodiment of an inventive locking means for use in carrying out the method of the invention.
Figure 5:
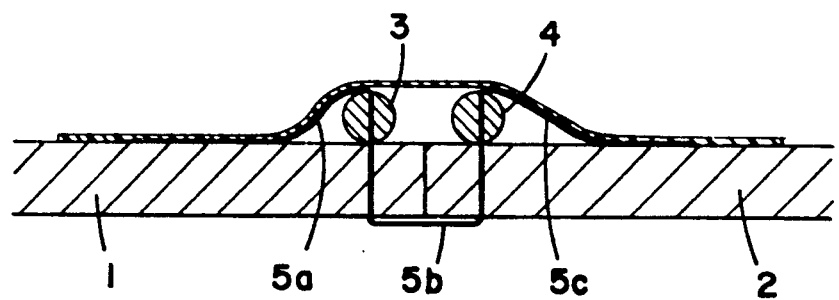
FIG. 5 is a cross-section view similar to FIG. 3, with taper over the elastic members.

For finally bringing together the skin edge portions 1, 2, one or both of the thread ends 5a, 5c; 6a, 6c of each suture thread 5 and 6, respectively, are pulled upwards relative to the respective rod 1, 2 while these are being maintained in constant engagement against the upper face of the respective skin edge portions 1, 2, such that central portions 5b, 6b etc., of the suture threads 5, 6 etc., located between the rods 3, 4 are shortened. Thus, the subcutaneous layer and the skin can then be adapted perfectly, yielding a surgical closure as schematically shown in FIG. 3. Normally, no knotting is required and the tension can easily be adjusted intra- and post-operatively. If the length of the rod is about 10 cm, only –5 sutures are needed. An optional final step consists in covering the whole incision area with a tape of the Mefix type. After 3-6 days, the suture threads can be removed and replaced by transverse strips of surgical tape.

An extremely important advantage of the inventive method is that the suture threads can be removed without causing any perceptible pain to the patient. The suture threads 5, 6 and the two locking members 3, 4 are preferably removed in the following way. In a first step, the suture threads are cut off with a pair of scissors on one side of the closure just between the skin and the rod. Thereafter, by gently pulling in the other rod, all suture threads are removed simultaneously.

While an illustrative embodiment of a method for providing a surgical closure and a locking means for use in carrying out the method has been shown and described above, it will be appreciated that the invention is not limited thereto. Accordingly, any modification, variation or equivalent arrangement within the scope of the accompanying claims should be considered to fall within the scope of the invention. For instance, the elongate rods 1, 2 as illustrated in the drawing may be replaced by elastic elements of any suitable shape, such as spherical ones for sewing small wounds. Further, it lies within the scope of the invention to knot together the thread end portions 5a and 5c above the rods 3, 4 in FIG. 3 in the event the skin edge portions 1 and 2 must be held together by such tension forces as are required to prevent any unintentional displacement between the thread and the rod.

What I claim and desire to secure by Letters Patent is:

1. A method for performing a surgical closure of a open skin incision or wound presenting two opposite skin edge portions to be held together, comprising the steps of sewing at least one suture thread through each one of said two skin edge portions and through each one of two separate elastic members associated with a respective one of said skin edge portions and arranged at the outside thereof, said elastic members being made of such a material that, when said suture thread is sewn therethrough frictional forces are established between said members and said suture thread, bringing together said two skin edge portions using said suture thread, so that frictional forces alone prevent movement of the thread within the members without the need to knot the thread, said elastic members being positioned in such a relation to said suture thread that after completion of said closure, each of said elastic members is being held in contact against the respective skin edge portion by a tensioned portion of said suture thread and said skin edge portions are being held together by said tensioned portion of said suture thread.

2. Method as claimed in claim 1, wherein the step of sewing includes sewing one end of said suture thread first through one of said elastic members, then through one of said skin edge portions, thereafter through the other of said skin edge portions, and finally through the other of said elastic members.

3. Method as claimed in claim 1, wherein said step of bringing together said two skin edge portions is performed at least partially after said suture thread has been sewn through each of said elastic members.

4. Method as claimed in claim 1, wherein each of said two elastic members comprises of an elongate elastic rod having a length which preferably is at least equal to the length of said incision or wound, the method further comprising the step of positioning each of said two rods in parallel with the respective skin edge portion, and wherein said step of sewing includes the step of sewing through each one of said skin edge portions and each one of said rods at a plurality of points distributed at intervals along the length of said rods.

5. Method as claimed in claim 4, wherein a separate suture thread is used for each of said points.

6. Method as claimed in claim 4, wherein each of said elastic rods is of generally circular cross-section and has circumferentially opposite guiding marks, and wherein the step of sewing includes sewing diametrically through said rods by using said guiding marks.

7. Method as claimed in claim 4, wherein said guiding marks comprise colored lines coinciding with generatrices of said rods.

8. Method as claimed in claim 4, wherein said guiding marks comprise grooves coinciding with generatrices of said rods.

9. Method as claimed in claim 1, further comprising a final step of applying an adhesive tape over said two elastic members.

10. Method as claimed in claim 1, wherein silicon rubber is used as material for said elastic members.

* * * * *

UNITED STATES PATENT AND TRADEMARK OFFICE
CERTIFICATE OF CORRECTION

PATENT NO. : 5,009,663
DATED : April 23, 1991
INVENTOR(S) : Albert Broome

It is certified that error appears in the above-identified patent and that said Letters Patent is hereby corrected as shown below:

On column 3, line 10 "shown" should be --sewn--.

On column 4, line 15 "-5" should be --4-5--.

On column 4, line 58 insert --,-- after the word "therethrough".

Signed and Sealed this

Eighth Day of December, 1992

*Attest:*

DOUGLAS B. COMER

*Attesting Officer*  *Acting Commissioner of Patents and Trademarks*